United States Patent
Schlienger et al.

(10) Patent No.: US 8,465,489 B2
(45) Date of Patent: Jun. 18, 2013

(54) SURGICAL NAIL

(75) Inventors: André Schlienger, Arlesheim (CH);
Markus Buettler, Oensingen (CH);
Peter Senn, Waldenburg (CH);
Christian Raehle, Basel (CH)

(73) Assignee: Synthes USA, LLC, West Chester, PA (US)

( * ) Notice: Subject to any disclaimer, the term of this patent is extended or adjusted under 35 U.S.C. 154(b) by 1620 days.

(21) Appl. No.: 11/301,760

(22) Filed: Dec. 12, 2005

(65) Prior Publication Data
US 2006/0161155 A1 Jul. 20, 2006

Related U.S. Application Data

(63) Continuation of application No. PCT/CH03/00375, filed on Jun. 12, 2003.

(51) Int. Cl.
*A61B 17/72* (2006.01)
(52) U.S. Cl.
USPC .......................................................... 606/62
(58) Field of Classification Search
USPC ........ 606/62–68, 96, 98, 329, 331; 623/23.23
See application file for complete search history.

(56) References Cited

U.S. PATENT DOCUMENTS

| | | | |
|---|---|---|---|
| 2,834,342 | A | 5/1958 | Yost |
| 3,255,747 | A | 6/1966 | Cochran et al. |
| 3,433,220 | A | 3/1969 | Zickel |
| 4,095,591 | A | 6/1978 | Graham, Jr. et al. |
| 4,103,683 | A | 8/1978 | Neufeld |
| 4,172,452 | A | 10/1979 | Forte et al. |
| 4,274,163 | A | 6/1981 | Malcom et al. |
| 4,438,762 | A | 3/1984 | Kyle |

(Continued)

FOREIGN PATENT DOCUMENTS

| | | |
|---|---|---|
| CH | 668 173 | 12/1988 |
| CH | 674 613 | 6/1990 |

(Continued)

OTHER PUBLICATIONS

International Search Report for International Application No. PCT/CH03/00375, mailed Feb. 19, 2004, German language version.

(Continued)

*Primary Examiner* — Jan Christopher Merene
*Assistant Examiner* — Steven Cotroneo
(74) *Attorney, Agent, or Firm* — Fay Kaplun & Marcin, LLP

(57) ABSTRACT

A surgical nail in the form of an intramedullary nail with a central axis, consisting of a material M with the tensile strength $F_z$, the compression strength $F_d$, the density $\rho_2$ and the modulus of elasticity E. The nail has at least at least one transverse borehole extending transversely to the central axis with the cross-sectional profile F, where the cross-sectional profile F has a maximum length a in the direction of the central axis and a maximum width b perpendicularly thereto. The nail also includes a longitudinal bore, which extends coaxially with the central axis, and a wall, as well as an insert with a longitudinal axis, which can be introduced within the longitudinal bore of the nail into the region of the transverse borehole. The insert is formed of a material m, which has a lower modulus of elasticity e<E than does the material M.

20 Claims, 2 Drawing Sheets

U.S. PATENT DOCUMENTS

| | | | | |
|---|---|---|---|---|
| 4,494,535 | A | 1/1985 | Haig | |
| 4,612,920 | A | 9/1986 | Lower | |
| 4,621,628 | A | 11/1986 | Brudermann | |
| 4,622,959 | A | 11/1986 | Marcus | |
| 4,657,001 | A | 4/1987 | Fixel | |
| 4,697,585 | A | 10/1987 | Williams | |
| 4,705,027 | A | 11/1987 | Klaue | |
| 4,754,749 | A | 7/1988 | Tsou | |
| 4,776,330 | A | 10/1988 | Chapman et al. | |
| 4,791,918 | A | 12/1988 | Von Hasselbach | |
| 4,817,591 | A | 4/1989 | Klaue | |
| 4,973,332 | A | 11/1990 | Kummer | |
| 5,032,125 | A | 7/1991 | Durham et al. | |
| 5,041,114 | A | 8/1991 | Chapman et al. | |
| 5,041,115 | A | 8/1991 | Frigg et al. | |
| 5,120,171 | A | 6/1992 | Lasner | |
| 5,167,663 | A | 12/1992 | Brumfield | |
| 5,176,681 | A | 1/1993 | Lawes et al. | |
| 5,263,955 | A * | 11/1993 | Baumgart et al. | 606/63 |
| 5,300,074 | A | 4/1994 | Frigg | |
| 5,312,406 | A | 5/1994 | Brumfield | |
| 5,364,398 | A | 11/1994 | Chapman et al. | |
| 5,454,813 | A * | 10/1995 | Lawes | 606/62 |
| 5,484,439 | A | 1/1996 | Olson et al. | |
| 5,549,610 | A | 8/1996 | Russell et al. | |
| 5,569,249 | A * | 10/1996 | James et al. | 606/62 |
| 5,573,536 | A | 11/1996 | Grosse et al. | |
| 5,578,035 | A | 11/1996 | Lin | |
| 5,591,168 | A | 1/1997 | Judet et al. | |
| 5,653,709 | A * | 8/1997 | Frigg | 606/64 |
| 5,658,287 | A | 8/1997 | Hofmann et al. | |
| 5,658,339 | A | 8/1997 | Tronzo et al. | |
| 5,713,901 | A | 2/1998 | Tock | |
| 5,713,902 | A | 2/1998 | Friedl | |
| 5,728,099 | A | 3/1998 | Tellman et al. | |
| 5,741,256 | A | 4/1998 | Bresina | |
| 5,772,662 | A | 6/1998 | Chapman et al. | |
| 5,908,422 | A | 6/1999 | Bresina | |
| 5,928,235 | A | 7/1999 | Friedl | |
| 5,935,127 | A | 8/1999 | Border | |
| 5,976,139 | A | 11/1999 | Bramlet | |
| 6,010,506 | A | 1/2000 | Gosney et al. | |
| 6,059,785 | A | 5/2000 | Schavan et al. | |
| 6,106,528 | A * | 8/2000 | Durham et al. | 606/64 |
| 6,123,708 | A | 9/2000 | Kilpela et al. | |
| 6,126,661 | A | 10/2000 | Faccioli et al. | |
| 6,187,007 | B1 | 2/2001 | Frigg et al. | |
| 6,228,086 | B1 * | 5/2001 | Wahl et al. | 606/67 |
| 6,296,645 | B1 | 10/2001 | Hover et al. | |
| 6,454,810 | B1 | 9/2002 | Lob | |
| 6,607,531 | B2 * | 8/2003 | Frigg | 606/62 |
| 6,709,436 | B1 * | 3/2004 | Hover et al. | 606/62 |
| 6,783,529 | B2 * | 8/2004 | Hover et al. | 606/62 |
| 7,182,765 | B2 | 2/2007 | Roth et al. | |
| 2001/0012939 | A1 * | 8/2001 | Wahl et al. | 606/67 |
| 2002/0151898 | A1 * | 10/2002 | Sohngen et al. | 606/62 |
| 2002/0173792 | A1 | 11/2002 | Severns et al. | |
| 2003/0069581 | A1 | 4/2003 | Stinson et al. | |
| 2003/0114855 | A1 | 6/2003 | Wahl et al. | |
| 2006/0064095 | A1 | 3/2006 | Senn et al. | |
| 2006/0111716 | A1 | 5/2006 | Schlienger et al. | |
| 2006/0149248 | A1 | 7/2006 | Schlienger et al. | |
| 2006/0189988 | A1 | 8/2006 | Schlienger et al. | |
| 2006/0235395 | A1 | 10/2006 | Frigg et al. | |
| 2006/0241605 | A1 | 10/2006 | Schlienger et al. | |
| 2008/0262496 | A1 | 10/2008 | Schlienger et al. | |

FOREIGN PATENT DOCUMENTS

| | | |
|---|---|---|
| DE | 196 29 011 A1 | 1/1998 |
| DE | 199 45 611 A1 | 9/2001 |
| DE | 103 20 855 | 8/2008 |
| EP | 0 251 583 A2 | 1/1988 |
| EP | 0 321 170 B1 | 6/1989 |
| EP | 0 381 462 A2 | 8/1990 |
| EP | 0 411 273 A1 | 2/1991 |
| EP | 0 471 418 A1 | 2/1992 |
| EP | 0 838 199 A1 | 4/1998 |
| EP | 0 845 245 A2 | 6/1998 |
| EP | 0 853 923 A1 | 7/1998 |
| EP | 0 919 200 A1 | 6/1999 |
| EP | 0 968 685 A2 | 6/1999 |
| EP | 1 053 718 A1 | 11/2000 |
| EP | 1 214 914 A2 | 6/2002 |
| EP | 1 260 188 A1 | 11/2002 |
| FR | 2 784 283 | 4/2000 |
| GB | 2209947 A | 6/1989 |
| JP | 09-066059 | 3/1997 |
| JP | 09-066060 | 3/1997 |
| JP | 09-066061 | 3/1997 |
| JP | 11-137566 | 5/1999 |
| JP | 2000-051224 | 2/2000 |
| JP | 2000-051225 | 2/2000 |
| JP | 2000-342596 | 12/2000 |
| WO | WO 93/15679 | 8/1993 |
| WO | WO 96/15737 | 5/1996 |
| WO | WO 97/37606 | 10/1997 |
| WO | WO 98/05263 | 2/1998 |
| WO | WO 98/30164 | 7/1998 |
| WO | WO 98/41161 | 9/1998 |
| WO | WO 98/46169 | 10/1998 |
| WO | WO 00/67653 | 11/2000 |
| WO | WO 02/060331 | 8/2002 |
| WO | WO 03/015649 | 2/2003 |

OTHER PUBLICATIONS

International Search Report for International Application No. PCT/CH03/00375, mailed Feb. 19, 2004, English language translation of the German language version.

International Preliminary Examination Report for International Application No. PCT/CH03/00375, completed Mar. 30, 2005, German language version.

International Preliminary Examination Report for International Application No. PCT/CH03/00375, completed Mar. 30, 2005, English language translation of the German language version.

* cited by examiner

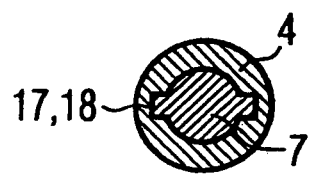
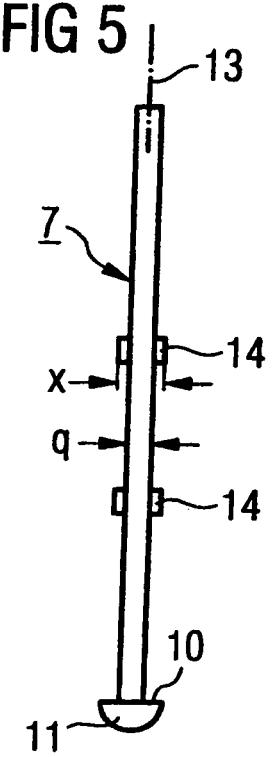
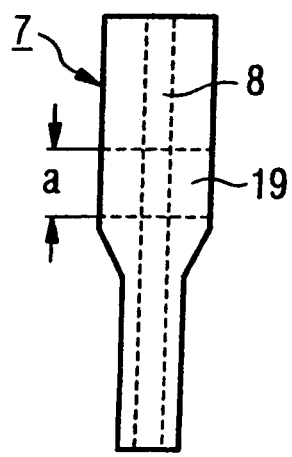
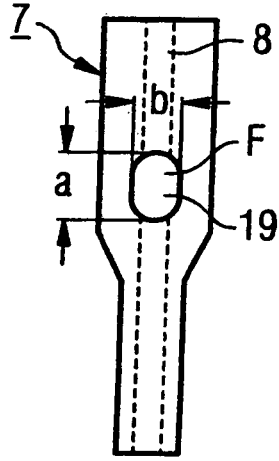
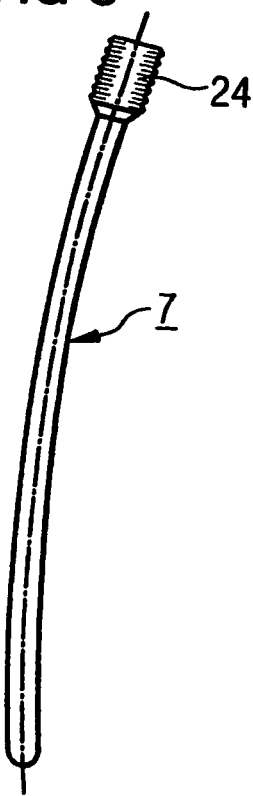

SURGICAL NAIL

RELATED APPLICATION DATA

The present application is a continuation of the U.S. National Stage designation of co-pending International Patent Application No. PCT/CH2003/000375, filed Jun. 12, 2003, the entire content of which is expressly incorporated herein by reference thereto.

FIELD OF INVENTION

The invention relates to a surgical nail, especially to a hollow intramedullary nail with a longitudinal central axis and at least one transverse borehole, and having a rod-shaped insert adapted for insertion within the hollow of the intramedullary nail in the region of the transverse borehole.

BACKGROUND OF THE INVENTION

The locking of intramedullary nails is known in the art. One or more locking screws or locking bolts (in the following, only the expression, a locking screw, is used; however, it is intended to include also the expression, locking bolt) are inserted into the transverse boreholes of the intramedullary nail either with the help of an imaging method (X-ray control) or a relatively complicated targeting device. In both cases, a certain targeting inaccuracy cannot be avoided, that is, the tip of the screw cannot be aligned precisely coaxially with the central axis of the transverse borehole and, instead, deviates therefrom by a certain amount. The external diameter of the screw is underdimensioned relative to the diameter of the transverse borehole so that, in spite of this targeting error, the locking screw ends up in the transverse borehole and can be brought through this borehole. If the targeting inaccuracy remains within the scope of this underdimensioning, the locking screw can be passed through the transverse boreholes without any problems in spite of this targeting error. However, because of the underdimensioning, the locking screw now has a certain clearance relative to the transverse borehole.

This clearance defines the amount by which the main bone fragments, which are to be locked by means of the locking screws in the corresponding locking hole, can move relative to the nail and accordingly, because of the rigidity of the nail, also relative to the other main fragments of the bone fastened with the same nail. Admittedly, this clearance is unavoidable in order to guarantee the applicability of the locking for the surgeon. However, it is clinically undesirable for certain indications, for example, in the case of metaphysical fragments.

Even nails with a solid cross-section, which may have an internal thread in the locking hole, are not free of clearance. The internal thread merely prevents the nail from shifting axially on the locking screw.

From U.S. Pat. No. 6,296,645, a hollow, intramedullary metal nail is known, which has one or two plastic inserts, through which the locking screw can be introduced, in the casing openings of the transverse borehole, which are diametrically opposite to one another and are referred to as windows. It is a disadvantage of this known medullary nail that the window-like plastic inserts can be pressed in under the stresses occurring during clinical use, so that the desired function is lost. However, even if the manipulations are carried out very carefully, the two plastic inserts could be pressed out of their "window" when the locking screw is passed through, which also leads to a loss of function.

SUMMARY OF THE INVENTION

The invention intends to remedy this problem. It is an object of the invention to create a surgical nail, especially an intramedullary nail, with which the clearance, existing between it and the locking screw, can be eliminated without risk and an improved holding force between the locking screw and the medullary nail can be achieved, without requiring higher precision from the user during the procedure.

Pursuant to the invention, this objective is accomplished with a surgical nail having a nail body with a central axis, a proximal end, a distal end, and a wall surrounding a longitudinal bore extending along the central axis, the nail body formed of a material M. A plurality of transverse boreholes extend through the nail transversely to the central axis, each transverse borehole having a cross-sectional profile F and a transverse axis, where the cross-section F has a maximum length $\alpha$ in the direction of the central axis and a maximum width b perpendicularly thereto. An elongate insert is configured and dimensioned for insertion along the central axis into the longitudinal bore of the nail in the area of the transverse boreholes.

With these, the following advantages can be achieved:

a) the targeting accuracy is not affected when the locking screw is introduced;

b) the nail and the insert can be packaged separately in a sterile manner and the surgeon can elect to use the nail with or without the insert. In the former case, the surgeon himself can introduce the insert into the nail and, optionally, also remove it once again. If the surgeon uses the nail without an insert, the latter remains sterile in its package for a next use. The doctor accordingly can decide during the operation whether or not to use an angularly stable locking of the locking screw, the concept of "angularly stable" denoting a limitation of certain degrees of freedom;

(c) the possibility of fixing bone fragments in an angularly stable manner in certain directions for a certain amount of the load.

In accordance with a preferred further development of the invention, the insert is constructed rod-shaped and can be introduced through the longitudinal borehole of the nail into the region of the transverse boreholes. The surgeon can insert the insert even after the nail has been implanted (without an insert), in that the insert is pushed forward from proximal direction into the longitudinal borehole as far as the region of the transverse boreholes.

The material m of the insert preferably has a lesser compressive strength $f_d < F_d$ as well as a lesser tensile strength $f_z < F_z$ than the nail material M. The modulus of elasticity "e" of the insert preferably is less than 0.8 E and typically less than 0.7 E, where E is the modulus of elasticity of the nail material M.

In one preferred embodiment, the material m of the insert consists of a biocompatible plastic, preferably a polyethylene or a high molecular weight polyethylene (HMWPE). This has the advantage that there is no breakdown of the plastic with unknown breakdown products.

In the case of an alternative, a material of lesser hardness, which is brought into the longitudinal borehole of the hollow nail, consists of a bioabsorbable plastic, which preferably is a polylactide. For this embodiment, initially there is a clearance-free transverse locking of the medullary nail, which then, with increasing absorption of the polymer, is gradually reduced, so that the transverse locking screw becomes movable once again relative to the medullary nail and, with that, also the bone fragments, which have been treated. Accordingly, after the fracture has consolidated, there is a dynamization of the bone fragments.

A further advantage of the bioabsorbable material consists therein that the chips, which result when a locking screw is screwed through the nail, can be broken down by the body.

In the case of a further embodiment, the nail has at least two transverse boreholes and preferably at least three transverse boreholes. One of the transverse boreholes may also be constructed as an elongated hole with the cross-sectional profile F, the longer dimension α of the elongated hole being disposed in the axial direction of the nail.

The material m of the insert preferably also has a density $\rho_1$, which is less than the density $\rho_2$ of the material M, $\rho_1$ preferably being less than 0.8 $\rho_2$.

The nail may comprise a locking screw or a locking bolt, which can be introduced into the transverse borehole (with cross-sectional profile F) and through the insert, and the external thread or threadless shaft of which has an external diameter d, which fulfills the condition α>d<b.

In the case of a further embodiment, the rod-shaped insert has a central longitudinal borehole.

The diameter of the longitudinal borehole of the nail may vary in the direction of its central axis and the longitudinal borehole preferably has a circular offset.

In the case of a further embodiment, the rod-shaped insert may also have a depression, which extends radially and transversely to its longitudinal axis. Due to this depression, a locking screw or a locking bolt can be centered and drilled through the insert more easily and fewer shavings of the material m result. The insert may also have several depressions, which are disposed in the same way as the transverse boreholes of the nail.

In the case of a further embodiment, the rod-shaped insert may be constructed conically. Due to this shape, the insert can be introduced more easily from the distal direction into the longitudinal borehole of the nail and, moreover, a press fit is possible.

In the case of a further embodiment, the rod-shaped insert and the wall of the nail have interacting means, preferably in the form of a groove and an projection, which fits into the groove, the interacting means fixing the insert rotatively in a previously specified position relative to the nail.

The rod-shaped insert may have one or more projections, extending radially and transversely to its longitudinal axis. These projections may be disposed similarly to the transverse boreholes in the nail. The projections have a transverse extent x, which advantageously fulfills the condition 1<x/q<2, q being the diameter of the insert (7). The advantage of this embodiment consists therein that, when the insert is introduced into the longitudinal borehole of the nail, the elevations snap into the transverse boreholes, so that the insert is positioned accurately and securely in the nail. Moreover, the increased displacement volume leads to an improved holding force, that is, to an increased angular stability.

The nail may be made available to the surgeon with an insert already introduced into its longitudinal borehole up into the region of the transverse boreholes or, alternatively, the nail and insert may be provided as separately packaged parts.

The nail may be used together with a locking screw with a screw shaft and an external thread. For the diameter d of the screw thread, a>d<b. Preferably, d is at least 5% smaller than the smaller of the two dimensions a, b.

To produce the nail, a solid of a material m can be introduced into the longitudinal borehole of the nail from the upper or lower end of the latter (made from the material M), so that the solid comes to rest at least in the region of one of the transverse boreholes of the nail.

BRIEF DESCRIPTION OF THE DRAWINGS

The invention and further developments of the invention are described in even greater detail in the following by means of partly diagrammatic representations of several embodiments, in which:

FIG. 4 shows a transverse section through the medullary nail in the region of the transverse borehole with a rotation-securing insert;

FIG. 5 shows a view of a rotation-securing insert of biocompatible plastic for insertion from the distal direction into a hollow medullary nail with radial projections corresponding to the position of the transverse boreholes in the medullary nail;

FIG. 6 shows a longitudinal section through an insert of biocompatible plastic for introduction from the proximal direction into a hollow medullary nail;

FIG. 7 shows a longitudinal section, rotated through 90°, through the insert of FIG. 6; and FIG. 8 shows a view of an insert for introduction from the proximal direction over the whole length of the hollow medullary nail.

DETAILED DESCRIPTION OF THE PREFERRED EMBODIMENTS

Figure 1:
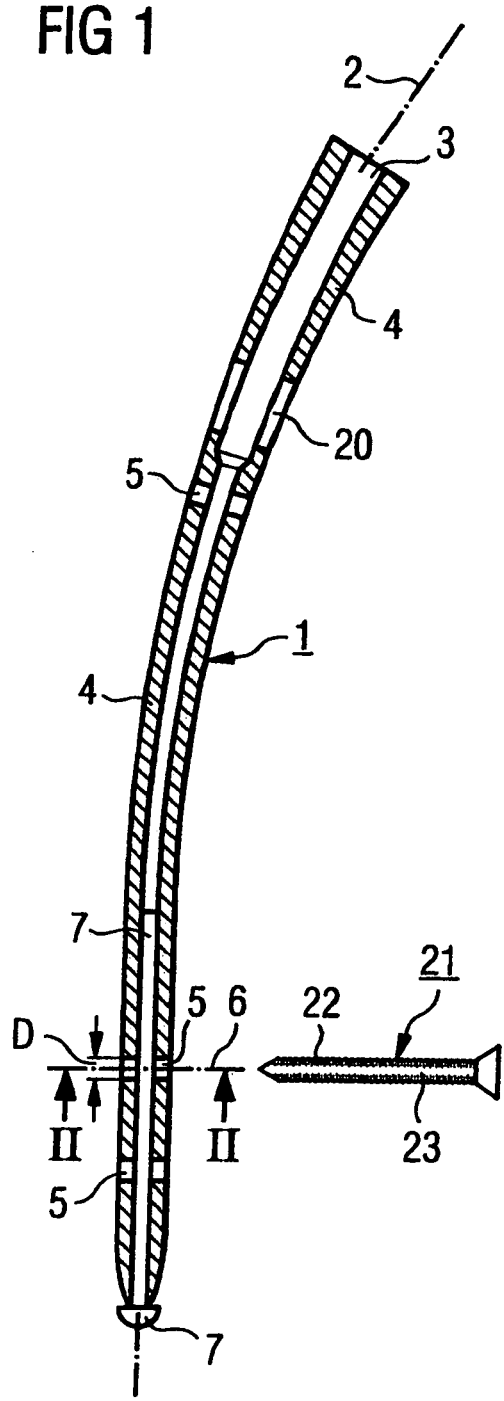
FIG. 1 shows a longitudinal section through a hollow medullary nail, partially filled with a softer material.

The surgical nail 1, shown in FIG. 1, is an intramedullary nail for tubular bones with a central axis 2, the nail consisting of a material M (metal or metal alloy) and having three transverse boreholes 5, which extend transversely to the central axis 2, a diameter D and a transverse axis 6. A fourth transverse borehole is mounted proximally and constructed as an elongated hole 20, the longer dimension being disposed in the axial direction. Two of the three transverse boreholes 5 are provided in the distal part of the medullary nail 1. Coaxially with the central axis 2, the medullary nail has a longitudinal borehole 3 and, as a result, a wall 4. A rod-shaped insert 7 (FIG. 3), in the form of a one-piece solid of absorbable polylactide, is inserted into this longitudinal borehole 3, so that, in the region of the two distal transverse boreholes 5, the longitudinal borehole 3 is filled with an accurately fitting material m of lower strength, especially with a lower modulus of elasticity (in comparison to the material M of the medullary nail). However, a press fit of the material m is also possible.

As shown in FIG. 1, a locking screw 21 with the shaft 22 and the external thread 23 can be screwed into the transverse borehole 5 and, with that, through the insert 7.

The insert 7 has a longitudinal borehole 8, which extends coaxially with its longitudinal axis 13. At its distal end, it has a hemispherical expansion 11 with a proximally directed stop 10. A secure, axial positioning of the insert 7 in the longitudinal borehole 3 of the medullary nail is guaranteed by the stop 10 of the expansion 11.

Figure 2:
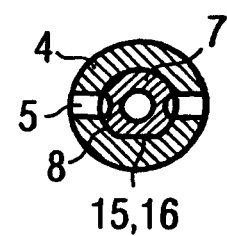
FIG. 2 shows a cross-section of the medullary nail in the region of the transverse borehole.

The insert 7 has four depressions 12, which extend radially and transversely to the longitudinal axis 13 and are disposed axially, so that they are level with the transverse boreholes 5 of the medullary nail, when the insert 7 is introduced into the longitudinal borehole 3 up to the stop 10. So that the depressions 12 are also aligned radially with the boreholes 5, the insert 7, as shown in FIG. 2, has a profile 15, which corresponds with a profile 16 in the longitudinal borehole 3 of the medullary nail, so that the insert 7 can be introduced into the longitudinal borehole 3 only in a certain rotative position.

As shown in FIG. 4, the insert 7 and the longitudinal borehole 3 of the medullary nail may also have two ribs/grooves 17, 18 instead of the profiles 15, 16 in the form of flattenings. The ribs/grooves 17, 18 bring about the same rotation-blocking effect.

Figure 3:
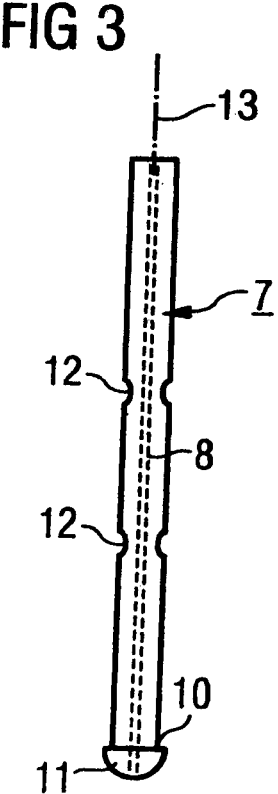
FIG. 3 shows an insert of a biocompatible plastic for the introduction from the distal direction into a hollow medullary nail with radial countersinkings or boreholes corresponding to the position of the transverse boreholes in the medullary nail.

In FIG. 5, an alternative to the insert 7 of FIG. 3 is shown, for which, instead of depressions 12, projections 14 are present, which, due to their elasticity, can be snapped into the openings of the transverse boreholes 5 in the wall 4, so that an axial and rotational securing of the insert 7 can also be achieved. The transverse extent x of the elevations 14 is subject to the condition that $1<x/q<2$, q being the diameter of the insert 7.

In FIGS. 6 and 7, a further, alternative insert 7 is shown, which can be introduced from the proximal direction, instead of the distal direction, into the longitudinal borehole 3 of the medullary nail. It has an axial longitudinal borehole 8, as well as an elongated hole 19, which corresponds to the elongated hole 20 in the medullary nail 1. The borehole 19 is approximately elliptical, with a long axis a and a short axis b.

A further embodiment of the insert 7 is shown in FIG. 8 and has approximately the same length as the medullary nail and, accordingly, covers all transverse boreholes 5 (locking boreholes) of the medullary nail from the proximal to the distal. The insert 7 is fixed by a thread 24 in the proximal region of the insert 7 in the hollow medullary nail. If necessary, the insert 7 can also be shortened during a surgical procedure.

What is claimed is:

1. An intramedullary nail comprising:
   a nail body having a central axis, a proximal end, a distal end, and a wall surrounding a longitudinal bore extending along the central axis, the nail body formed of a material M;
   a plurality of transverse boreholes extending transversely to the central axis, each transverse borehole having a cross-sectional profile F and a transverse axis, where the cross-section F has a maximum length a in the direction of the central axis and a maximum width b perpendicularly thereto; and
   an elongate insert configured and dimensioned for insertion along the central axis into the longitudinal bore of the nail in the area of the transverse boreholes, the insert having a longitudinal axis and formed of a material m along an entire length thereof and including an expansion at a distal end thereof, the material m having a modulus of elasticity e less than a modulus of elasticity E of the nail material M, and the expansion having a cross-sectional area larger than a cross-sectional area of the longitudinal bore at the distal end of the nail body to prevent the expansion from moving proximally into the longitudinal bore.

2. The nail of claim 1, wherein the insert is configured and adapted to interface with the wall of the nail to rotationally fix the insert in a predetermined position relative to the nail.

3. The nail of claim 2, wherein the insert includes a projection that mates with a groove on the wall of the nail.

4. The nail of claim 1, wherein the insert includes projections on an outer surface configured to interface with the transverse boreholes in the wall of the nail to secure the insert both axially and rotationally within the nail.

5. The nail of claim 1, wherein the nail includes at least three transverse boreholes.

6. The nail of claim 1, wherein the insert has a central longitudinal bore.

7. The nail of claim 1, wherein at least one of the transverse boreholes is constructed as an elongated slot having a cross-sectional profile F with the longer dimension a oriented along the central axis of the nail.

8. The nail of claim 1, further comprising a locking screw for introduction into the transverse borehole and through the insert, the locking screw having a shaft with an external diameter d, where $a>d<b$.

9. The nail of claim 1, wherein the longitudinal bore of the nail has a diameter that varies along the central axis of the nail.

10. The nail of claim 1, wherein the insert has at least one radial depression extending transversely to the longitudinal axis of the insert.

11. The nail of claim 1, wherein at least a portion of the insert has a conical shape.

12. The nail of claim 1, wherein the insert includes at least one radial projection extending transverse to the longitudinal axis.

13. The nail of claim 12, wherein the insert includes a plurality of radial projections adapted to interface with the transverse boreholes of the nail.

14. The nail of claim 13, wherein the insert has an outer diameter q, and the distance from an outer surface of one radial projection to an outer surface of another radial projection is x, where $1<x/q<2$, and q is the diameter of the insert.

15. The nail of claim 1, further comprising a locking screw with a screw shaft and an external thread, the screw thread having a diameter d where $a>d<b$.

16. An intramedullary nail comprising:
   a nail body having a central axis, proximal end, a distal end, and a wall surrounding a longitudinal bore extending along the central axis, the nail body formed of a material M;
   a plurality of transverse boreholes extending transversely to the central axis, each transverse borehole having a cross-sectional profile F and a transverse axis, where the cross-section F has a maximum length a in the direction of the central axis and a maximum width b perpendicularly thereto; and
   an elongate insert configured and dimensioned for insertion along the central axis into the longitudinal bore of the nail in the area of the transverse boreholes, the insert having a longitudinal axis and being formed of a material m along an entire length thereof and including an expansion at a distal end thereof, the material m having a modulus of elasticity e less than a modulus of elasticity E of the nail material M, wherein the insert is configured and adapted to interface with the wall of the nail to rotationally fix the insert in a predetermined position relative to the nail, and the expansion having a cross-sectional area larger than a cross-sectional area of the longitudinal bore at the distal end of the nail body to prevent the expansion from moving proximally into the longitudinal bore.

17. The nail of claim 16, wherein the insert includes projections on an outer surface configured to interface with the transverse boreholes in the wall of the nail to secure the insert both axially and rotationally within the nail.

18. The nail of claim 16, wherein at least one of the transverse boreholes is constructed as an elongated slot having a cross-sectional profile F with the longer dimension a oriented along the central axis of the nail.

19. The nail of claim 16, further comprising a locking screw for introduction into the transverse borehole and through the insert, the locking screw having a shaft with an external diameter d, where $a>d<b$.

20. A method for repairing bone fractures comprising:
introducing an intramedullary nail into the medullary canal of a bone, the nail having a central axis, proximal end, a distal end, and a wall surrounding a longitudinal bore extending along the central axis, the nail body formed of a material M and having a plurality of transverse boreholes extending transversely to the central axis;
inserting an elongate insert along the central axis into the longitudinal bore of the nail in the area of the transverse boreholes, the insert having a longitudinal axis and longitudinal bore and including an expansion at a distal end thereof, wherein the insert is formed of a material m, along an entire length thereof, the material m having a modulus of elasticity e less than a modulus of elasticity E of the nail material M, and the expansion having a cross-sectional area larger than a cross-sectional area of the longitudinal bore at the distal end of the nail body to prevent the expansion from moving proximally into the longitudinal bore;
aligning a drill with at least one transverse borehole of the nail to create a hole for a locking element; and
inserting a locking element through the transverse bore and through the insert to lock the nail in position.

* * * * *